US005189062A

United States Patent [19]

Szegö et al.

[11] Patent Number: 5,189,062

[45] Date of Patent: Feb. 23, 1993

[54] PLANT PROTECTING AGENT

[75] Inventors: András Szegö; László Pap; Lajos Nagy; Eva Somfai; György Szucsány, all of Budapest; István Székely, Dunakeszi; Anikó D. née Molnár; Ágnes Hegedus, both of Budapest, all of Hungary

[73] Assignee: Chinoin Gyogyszer -ES Vegyeszeti Termekek Gyara R.T., Budapest, Hungary

[21] Appl. No.: 827,514

[22] Filed: Jan. 28, 1992

Related U.S. Application Data

[63] Continuation-in-part of Ser. No. 459,773, Jan. 12, 1990, abandoned.

[30] Foreign Application Priority Data

Apr. 7, 1988 [HU] Hungary ............................. 1723/88

[51] Int. Cl.[5] ..................... A01N 37/34; A01N 43/08; A01N 53/00; A01N 57/00

[52] U.S. Cl. ..................................... 514/521; 514/84; 514/85; 514/86; 514/89; 514/91; 514/92; 514/93; 514/119; 514/120; 514/122; 514/127; 514/128; 514/129; 514/132; 514/147; 514/461; 514/473; 514/421; 514/531

[58] Field of Search ..................... 514/421, 84, 85, 86, 514/89, 91, 92, 93, 119, 120, 122, 127, 128, 129, 132, 147, 461, 473, 521, 531

[56] References Cited

U.S. PATENT DOCUMENTS

| | | | |
|---|---|---|---|
| 4,560,677 | 12/1985 | Dybas | 514/456 |
| 4,780,459 | 10/1988 | Matthewson | 514/521 |
| 4,963,584 | 10/1990 | Hidasi et al. | 514/521 |

*Primary Examiner*—Allen J. Robinson
*Attorney, Agent, or Firm*—Herbert Dubno; Jonathan Myers

[57] ABSTRACT

ULV plant protecting arthropodicidal formulation comprising alkyl aryl polyglycol ether as further additives in addition to the active ingredient(s) dissolved in the mixture of alphatic hydrocarbons and sunflower oil. The formulation according to the invention has an initial contact angle on the plant surface of $>13°$, after 20 minutes of $>6°$ and it is often 120 minutes still at least 2°.

8 Claims, No Drawings

PLANT PROTECTING AGENT

This is a continuation-in-part of co-pending application Ser. No. 07/459,773 filed on Jan. 12, 1990, now abandoned.

CROSS REFERENCE TO RELATED APPLICATION

This application is a national phase application of PCT/HU 89/00012 filed Apr. 7, 1989 and based upon Hungarian national application 1723/88 of Apr. 7, 1988 under the International Convention.

FIELD OF THE INVENTION

The invention relates to plant protecting anthropodicidal ULV formulations containing interfacial tension modifying materials as further additives.

BACKGROUND OF THE INVENTION

It is known that the LV (Low Volume) and ULV (Ultra Low Volume) spray application methods are the most advantageous and economical methods for plant and forest protection. These formulations are applied in a very small amount (5 l/ha) without dilution or in a low aqueous dilution (5–100 l/ha) instead of the common high rate (600 l/ha) or medium rate (100–600 l/ha) dilutions (Matthews G. A.: Pest management, 1984, Longman, London and New York). The advantage of said treatments is that no water is required to prepare the spray and sometimes the ULV formulations are more active than the emulsion concentrates containing the same dose of active ingredient (J. Econ. Entomol., 1986, 79:202).

However the treatments using a preparation in an amount less than 5 l/ha (i.e. the ULV treatments) can ensure the suitable coverage—which in turn ensures the effective control of the pests—only if the spraying is carried out in a correct, optimal drop size distributin. The optimal drop size plays very often a more important role than the dose used (J. Econ. Entomol., 1987. 80:460). Therefore special spray heads are generally used (e.g. Unirot, Autorot, Beecomist, MicroMax (DR4, Flak). The formulations are generally used without dilution and the active ingredient are dissolved in vegetable and/or mineral oils.

As mineral oil a mixture of aliphatic and aromatic hydrocarbons is used. The viscosity of the mineral oil does not exceed the value of 50 cP and the flash point is above 60° C. (e.g. paraffin oil, Risella 917, Solvesso 200, HAN, Exxsol D 60).

The efficiency of the contact insecticides is also influenced by the durability of the drop to be found on the surface of the plant. The oils used in the ULV formulations spread gradually on the surface then penetrate into the epicuticular layer of wax of the plant. By this means the contact surfaces between the plant and the spray drop—and so the actual surfaces for the resorption of the active ingredient into the plant—are increased, however the specific dose "available" for the insects may decrease which may slow down the intoxication.

It is known that the efficiency of the permethrin used in form of oily ULV formulation can be positively influenced by the retention time of the drop to be found on the surface of the leaf which can be followed by the change of the wetting angle (contact angle) (Pestic. Sci. 1984, 15:382). The wetting angle depends on the surface tension of the solid and liquid phases, on the interfacial tension and on the surface roughness (Szántó, P: The basis of the Collidal Chemistry, 1987, Publisher: Gondolat, Budapest).

SUMMARY OF THE INVENTION

The invention relates to ULV plant protecting anthropodicidal formulations suitable for application in a very small amount, comprising 0.5–30 g/l of synthetic pyrethroids and/or phosphoric acid esters, thiophosphoric acid esters and/or dithiophosphoric acid esters in an amount of 0.5–300 g/l dissolved in a mixture comprising 2–300 g/l aliphatic hydrocarbons, and sunflower oil in an amount necessary to reach 1000 ml and comprising further alkylaryl polyglycol ether in an amount of 2–100 g/l, preferably 15–60 g/l as an additive ensuring that the initial wetting (contact) angle of the formulation on the plant surface is greater than 13°, it is greater than 6° after 20 minutes and it is at least 2° after 120 minutes.

DETAILED DESCRIPTION OF THE INVENTION

The aim of our invention is to provide spray drops having a lengthened retention time by influencing the above mentioned factors and thereby to improve the efficacy of the ULV formulations.

The present invention is based on the recognition that the efficacy of certain ULV compositions in oil or in mixture of oils can be enhanced if said compositions contain suitable components for the modification of the penetration. The known ULV formulations used without dilution do not contain additives tensides for decreasing the interfacial tension.

The invention relates to ULV plant protecting anthropodicidal formulations suitable for application in a very small amount, comprising 0.5–30 g/l of synthetic pyrethroids, and/or phosphoric acid esters, thiophosphoric acid esters and/or dithiophosphoric acid esters in an amount of 0.5–300 g/l, dissolved in a mixture comprising 2–300 g/l aliphatic hydrocarbons and sunflower oil in an amount necessary to 1000 ml and comprising further alkylaryl polyglycol ether in an amount of 2–100 g/l, preferably 15–60 g/l as additive ensuring that the initial wetting (contact) angle of the formulation on the plant surface is greater than 13°, it is greater than 6° after 20 minutes and it is at least 2° after 120 minutes.

The formulations according to the invention contain the following natural or synthetic pyrethroids: allethrin, bifenthrin, bioallethrin, bioresmethrin, chinmix, cyfluthrin, cyhalothrin, cypermethrin, deltamethrin, fenpropethrin, fenvalerate, flycythrinate, fluvalinate, permethrin, phenothrin, resmethrin, tetramethrin, tralomethrin, and/or transmix.

The formulations according to the invention contain the following phosphoric acid esters: trichlorfon, propaphos, dicrotophos, phosphamidon, profenophos; the following thiophosphoric acid esters: acephate, parathion, methylparathion, chlorpyriphos, methamidophos, demeton, oxy-demeton-methyl, fenitrotion, EPN, triazophost, pirimiphos-ethyl, mevinphos, quinalpos, fenthion, pirimiphos-methyl and/or the following dithiophosphoric acid esters: dimethoate, azinphos-methyl, azinphos-ethyl, phosmet, malathion, phenthoate, methidathion and/or phosalon.

In the formulation according to the invention preferably nonylphenol polyglycol ether (EO=6–10) is used as alkylaryl polyglycol ether and the aliphatic hydrocarbon mixture is preferably a mixture of $C_{10-15}$ hydrocarbons containing 45-50% raphthene and having a flash point higher than 58° C.

The oil used in the preparation according to the invention is preferably a contamination-free, double-filtered sunflower oil (pharmacopeia).

Those compositions are the most effective which enable—due to the modifying components—the formation of such a contact angle which can ensure the adhesion of the drops located on a vertical or horizontal plant surface or on a plant surface between said two geometrical positions and can inhibit the absorption thereof within 2 hours.

The experimental data presented in the following Examples prove that the efficiency of these compositions surpasses that of the comparative compositions containing no modifying compound.

The contact (wetting) angle depends on the interfacial tension between the oil drop and the given plant surface further on the gravity related to the drop size (Pestic. Sci., 1987. 15:382) on the quality of the oil (Pestic. Sci., 1987. 20:241) and on different physical parameters, e.g. temperature, humidity (Pestic. Sci., 1987. 20:105). These all have an influence on the spreading of the drop and on the penetration of the active ingredient into the epicuticular layer of wax.

In the following Examples the behavior of drops having a diameter of 80 μm and prepared under constant physical parameters from a preferred oil mixture was examined on different plant surfaces in the presence of different penetration modifying materials used individually or in mixture.

During our experiments the mixtures of different vegetable oil, e.g. soya, rape, palm, sunflower oil and mineral oils, e.g. different aromatic and aliphatic hydrocarbons and the mixtures thereof were examined as solvent mixtures. As plant surface the young foliage leaves of lucerne (Medicago saliva) and sunflower (Helianthus annus) were used. The contact angle and absorption time of the plant protecting ULV formulations were determined by an optical method and the retention time was followed by the change of the contact angle in time.

It has been established that the contact angle of the solution obtained by the use of the mixture of sunflower oil and mixed hydrogenated aliphatic hydrocarbons is 7°-10°, however an even lower value (7°-1°) may be obtained by the use of other mixtures. Surprisingly even the penetration time of the compositions having a relatively great contact angle (10°) is only 15-20 minutes. The penetration of the ULV formulations having a contact angle below 7° takes place very quickly, in 2-15 minutes.

Accordingly such solvent mixture was used as starting solvent which shows—in the form of the ULV formulation—a contact angle of 7°-10°. The following composition meets this requirement:

0.5-30 g/l of pyrethroid and/or 0.5-300 g/l phosphoric acid ester 2-300 g/l of aliphatic hydrocarbon mixture sunflower oil to 1000 ml.

Using the above composition the contact angle measured on the surface of the plant model was 7°-10° and the penetration time was 15-20 minutes.

As aliphatic hydrocarbon mixture EXXSOL D 60 TM and EXXSOL D 100 TM products (mixture of $C_{10-15}$ hydrocarbons, naphthene content: 45-50%, flash point: 50°-100° C.) was used.

Exxsol ® D 60 has the following characteristics:

| | |
|---|---|
| Appearance, Visual | Bright & Clear |
| Aromatics Content, Liquid Chromatography, Vol % | 1.0 Max. |
| Color, Saybolt, ASTM D 156 | +30 Min. |
| Corrosion, Copper Strip, ASTM D 130 3 hours at 100° C. | 1 Max. |
| Distillation, ASTM D 86, °C. | |
| Initial Boiling Point | 182 Min. |
| 50% Recovered | 190-196 |
| Dry Point | 213 Max |
| Flash Point, ASTM D 56, °C. | 60 Min. |
| Sulfur Content, ASTM D 3120, ppm | 5 Max. |

| | | ASTM Test |
|---|---|---|
| VOLATILITY | | |
| Distillation, °C. (°F.) | | D 86 |
| IBP | 183 (362) | |
| 5% | 187 (368) | |
| 10% | 188 (370) | |
| 50% | 193 (379) | |
| 90% | 203 (397) | |
| 95% | 206 (403) | |
| DPT | 211 (411) | |
| Flash, TCC, °C. (°F.) | 61 (141) | D 56 |
| Evaporation, secs. | | D 3539 |
| 50 vol. % | 4000 | |
| 95 vol. % | 10200 | |
| Relative evaporation (NBA) | 0.06 | D 3539 |
| SOLVENCY | | |
| Aniline Pt, °C. (°F.) | 69 (156) | D 611 |
| Kauri-butanol value | 32.5 | D 1133 |
| Solubility Parameter | 7.6 | Calculated |
| COMPOSITION, VOLUME % | | (a) |
| Aromatics | 0.5 | |
| Naphthenes | 55.5 | |
| Paraffins | 44 | |
| Benzenes | <0.01 | |
| GENERAL | | |
| Auto Ignition Temp., °C. (°F.) | 227 (440) | E 659 |
| Color, Saybolt | +30+ | D 156 |
| Copper corrosion 3 hrs, @ 100° C. (212° F.) | 1A | D 130 |
| Density, kg/L @ 15° C. (59° F.) | 0.792 | D 1298 |
| Gravity, °API | 47.0 | D 287 |
| Non-Volatile Material, mg/100 mL | <1.0 | D 1353 |
| Refractive index @ 20° C. (68° F.) | 1.434 | D 1218 |
| Sulfur, Wt. ppm | <1 | D 3120 |
| Vapor Pressure, kPa (psia) @ 38° C. | 0.5 (0.07) | Calculated |
| Viscosity, mPa · s(cP) @ 25° C. | 1.24 | D 445 |

(a) by liquid chromatographic and mass spectrometric analysis

EXXSOL D 60 Solvent is almost fully dearomatized. By severe hydrogenation, the aromatics present in straight cut petroleum product are converted to naphthenes. Since naphthenes have better solvency than straight chain paraffins, the result is a product which better solvency than would by achieved by simple removal of aromatics. Hydrogenation also saturates olefins and removes impurities such as sulfur and halogens to yield and extremely stable product.

TYPICAL PHYSICAL & CHEMICAL PROPERTIES FOR EXXSOL ® D 60

SPECIFIC GRAVITY:
Not available
Density: 6.6 lbs/gal at 59
SOLUBILITY IN WATER, WT. % AT °F.:
Less than 0.10 at 68.
SP. GRAV. OF VAPOR, at 1 atm (Air=1):
Greater than 1.00
EVAPORATION RATE, n-Bu Acetate=1:
0.1
VAPOR PRESSURE, mmHg at °F.:
3 at 100

VISCOSITY OF LIQUID, CST AT °F.:
2 at 77
FREEZING/MELTING POINT, °F.:
32 Below
BOILING POINT, °F.:
360 to 419

TYPICAL PHYSICAL & CHEMICAL PROPERTIES FOR EXXSOL® D 100

SPECIFIC GRAVITY:
Not Available
Density: 6.8 lbs/gal at 59
SOLUBILITY IN WATER, WT. % AT °F.:
Less than 0.10 at 68
SP. GRAV. OF VAPOR, At 1 atm (Air=1):
Greater than 1.00
EVAPORATION RATE, n-Bu Acetate=1:
Less than 0.0
VAPOR PRESSURE, mmHg at °F.:
0 at 100
Less than 1 at 131
VISCOSITY OF LIQUID, CST AT °F.:
3 at 77
2 at 104
FREEZING/MELTING POINT, °F.:
Less than −4
BOILING POINT, °F.:
462 to 511

The sunflower oil used was of pharmacopeia quality, double filtered.

Several additives modifying the interfacial behavior were examined in different concentration, and the contact angle and the change thereof in time was determined on the leaves of lucerne and sunflower plants.

The following materials were used as penetration modifying components:

Ionic type materials:
- Ca salt of dodecylbenzenesulfonic acid,

Non-ionic type materials:
- fatty alcohol polyglycol ethers: compounds of formula $RX(CH_2CH_2O)_yH$, wherein if X=0, then RO=cocoanut oil alcohol, oleyl alcohol, pine oil alcohol, isotridecyl alcohol;
- alkyl-aryl polyglycol ethers, corresponding to the above general formula, wherein if R is alkyl phenol then it stands for nonylphenol or tributylphenol and y=2-12,
- fatty amine polyglycol ethers, wherein if X=NH then RNH is coconut oil, stearyl, oleyl, pine oil amine and y=2-12;
- propylene oxide-ethylene oxide block polymer (EO=10-12)

It has been found that the ULV formulations corresponding to the following composition:
- 0.5-30 g/l of pyrethroid and/or 0.5-300 g/l phosphoric acid ester,
- 2-300 g/l of mixed aliphatic hydrocarbon,
- 15-60 g/l of alkyl aryl polyglycol ether (EO=6-10) and
- sunflower oil to 1000 ml, have an initial contact angle on the surface of a plant model of 13°-21°, after 20 minutes of 6°-10° and after 120 minutes of 2°-3° and it decreases to 0° only after 180 minutes.

When using any other additives in a concentration of 15-60 g/l or the formulation tested contains no additives, the initial contact angle determined on the plant surfaces was smaller than 16° and 0° after 20 minutes in case of lucerne and smaller than 8° in case of maize and 0° after 120 minutes in both cases.

It will be proved by the following Examples that the penetration time of the spray drops can significantly be increased by the use of the alkyl aryl polyglycol ethers and this results in the significant increase of the efficiency of the active ingredient contained in the formulations. Due to this enhanced efficiency the specific dose (g active ingredient/ha) may be reduced which is very advantageous from point of view of the costs of the plant protection and of the moderation of the pesticide-load. The active ingredients available for a longer time as potent pesticides are further very advantageous as they may be utilized to control the resistant populations.

The definitions of the abbreaviations used in the following Tables are the following:

CIP=cypermethrin=alpha-cyano-3-phenoxy-benzyl-3-(2,2-dichlorovinyl)-2,2-dimethyl-cyclopropane carboxylate
CHX="chinmix"=a mixture in a ratio of 40:60 of the following isomers of cypermethrin: (IRcisS+1-ScisR):1RtransS+1Strans==40:60
QUI=quinalphos=0,0-diethyl-0-chinoxalin-2-yl-phosphorothioate
DIA=diazinon=0,0-diethyl-0-2-isopropyl-6-methyl-pirimidin-4-yl-phosphorothioate
TRIA=triazophos=0,0-diethyl-0-1-phenyl-1H-1,2,4-triazol-3-yl-phosphorothioate
MET=methidathion=S-2,3-dihydro-5-methoxy-2-oxo-1,3,4-thiadiazol-3-yl-methyl-0,0-dimethylphosphorodithioate
HEPT=heptenophos=chlorobicyclo[3,2,0]hepta-2,6-dien-6-yl-dimethylphosphate
PHOS=phosalone=S-6-chloro-2,3-dihydro-2-oxobenzeneoxazol-3-yl-methyl-0,0-diethyl-phosphorodithioate
SF=synergistic factor
PBO=piperonyl butoxide The invention is illustrated by the following Examples.

Example 1

| | | |
|---|---|---|
| Chinmix | | 7.5 g/l |
| Exxsol D 100 TM | | 250 g/l |
| Sunflower oil | to | 1000 ml |

The composition is prepared by using a technology generally known for preparing solutions, i.e. the sunflower oil is admixed with the Exxsol D 100 TM and the active ingredient is dissolved in the mixture obtained at 15°-30° C., thereafter the solution is stirred for 30 minutes.

The contact angle is determined using a microscope having a magnification of 30x and equipped with an optical cross spider. The displacement of the cross spider is determined by a fine scale angular displacement indicator.

| Wetting time | Contact angle lucerne | Contact angle sunflower |
|---|---|---|
| 0. minute | 10° | 6° |
| 20. minute | 0° | 8° |
| 120. minute | 0° | 0° |

Example 2

| | | |
|---|---|---|
| Chinmix | | 0.75 g/l |
| Exxsol D 100 TM | | 5 g/l |
| sunflower oil | to | 1000 ml |

The composition is prepared and the contact angle is determined as described in Example 1.

| Wetting time | Contact angle lucerne | Contact angle sunflower |
|---|---|---|
| 0. minute | 8° | 4° |
| 20. minute | 0° | 5° |
| 120. minute | 0° | 0° |

Example 3

| | | |
|---|---|---|
| Chinmix | | 7.5 g/l |
| Nonylphenol polyglycol ether (EO = 8) | | 60 g/l |
| Exxsol D 100 TM | | 250 g/l |
| sunflower oil | to | 1000 ml |

The composition is prepared by using the technology generally known for preparing solutions, i.e. the sunflower oil is admixed with the Exssol D 100 TM, thereafter the nonylphenol polyglycol ether is added, homogenized and the active ingredient is dissolved in the mixture thus obtained. The contact angle is determined as described in Example 1.

| Wetting time | Contact angle lucerne | Contact angle sunflower |
|---|---|---|
| 0. minute | 19° | 21° |
| 20. minute | 6° | 15° |
| 120. minute | 3° | 6° |

Example 4

| | | |
|---|---|---|
| Transmix | | 0.75 g/l |
| Nonylphenol polyglycol ether (EO = 8) | | 30 g/l |
| Exxsol D 100 TM | | 5 g/l |
| Sunflower oil | to | 1000 ml |

The composition is prepared as described in Example 3, and the contact angle is determined according to Example 1.

| Wetting time | Contact angle lucerne | Contact angle sunflower |
|---|---|---|
| 0. minute | 19° | 20° |
| 20. minute | 6° | 15° |
| 120. minute | 2° | 4° |

Example 5

| | | |
|---|---|---|
| Chinmix | | 7.5 g/l |
| Fatty alcohol polyglycol ether (EO = 2) | | 60 g/l |
| Exxsol D 100 TM | | 250 g/l |
| Sunflower oil | to | 1000 g/l |

-continued

The composition is prepared as described in Example 3 and the contact angle is determined according to Example 1.

| Wetting time | Contact angle lucerne | Contact angle sunflower |
|---|---|---|
| 0. minute | 9° | 4° |
| 20. minute | 6° | 2° |
| 120. minute | 0° | 0° |

Example 6

| | | |
|---|---|---|
| Chinmix | | 7.5 g/l |
| Alkyl aryl polyglycol ether (EO = 2) | | 30 g/l |
| Exxsol D 100 TM | | 250 g/l |
| Sunflower oil | to | 1000 g/l |

The composition is prepared as described in Example 3 and the contact angle is determined according to Example 1.

| Wetting time | Contact angle lucerne | Contact angle sunflower |
|---|---|---|
| 0. minute | 8° | 6° |
| 20. minute | 3° | 0° |
| 120. minute | 0° | 0° |

Example 7

To a measuring flask of 1000 ml, 240 g quinalphos and 35 g nonylphenol polyglycol ether (EO=10) are added and filled up to 1000 ml with the 1:5 mixture (v/v) of Exxsol D 100 TM and sunflower oil. The mixture obtained is homogenized at 50° C. in the flask and after complete dissolution is cooled to 20° C. The contact angle is determined as described in Example 1.

| Wetting time | Contact angle lucerne | Contact angle sunflower |
|---|---|---|
| 0. minute | 18° | 20° |
| 20. minute | 9° | 18° |
| 120. minute | 6° | 11° |

Example 8

In the mixture of 80 g piperonyl butoxide and 23 g nonylphenol polyglycol ether (EO=10) 10 g chinmix and thereafter 240 g quinalphos are dissolved at 45° C. The solution thus obtained is filled up to 1000 ml with the 1:6 mixture (v/v) of Exxsol D 60 TM and sunflower oil.

| Wetting time | Contact angle lucerne | Contact angle sunflower |
|---|---|---|
| 0. minute | 16° | 18° |
| 20. minute | 8° | 12° |
| 120. minute | 4° | 8° |

Example 9

| | | |
|---|---|---|
| Tetramethrin | | 10 g/l |
| Nonylphenol polyglycol ether (EO = 8) | | 60 g/l |
| Exxsol D 100 TM | | 250 g/l |
| Sunflower oil | to | 1000 ml |

The composition is prepared as described in Example 3 and the contact angle is determined according to Example 1.

| Wetting time | Contact angle lucerne | Contact angle sunflower |
|---|---|---|
| 0. minute | 17° | 23° |
| 20. minute | 7° | 15° |
| 120. minute | 3° | 7° |

Example 10

| | | |
|---|---|---|
| Cypermethrin | | 20 g/1 |
| Nonylphenol polyglycol ether (EO = 10) | | 15 g/l |
| Exxsol D 100 TM | | 200 g/l |
| Sunflower oil | to | 1000 ml |

The composition is prepared as described in Example 3 and the contact angle is determined according to Example 1.

| Wetting time | Contact angle lucerne | Contact angle sunflower |
|---|---|---|
| 0. minute | 17° | 24° |
| 20. minute | 11° | 10° |
| 120. minute | 8° | 8° |

Example 11

| | | |
|---|---|---|
| Cypermethrin | | 2 g/l |
| Nonylphenol polyglycol ether (EO = 10) | | 20 g/l |
| Exxsol D 100 TM | | 48 g/l |
| Sunflower oil | to | 1000 ml |

The composition is prepared as described in Example 3 and the contact angle is determined according to Example 1.

| Wetting time | Contact angle lucerne | Contact angle sunflower |
|---|---|---|
| 0. minute | 21° | 23° |
| 20. minute | 7° | 14° |
| 120. minute | 3° | 9° |

BIOLOGICAL EXAMPLES

Example 12

Activity on potato beetle

Petri dishes (0 9 cm) are lined with potato leaves originated from shoots which had not been treated with insecticides previously and sprayed with the compositions described above. The treatment is carried out with a spraying machine (ULVA-system) modified for laboratory purpose, having a rotating disc and equipped with a speed governor. On an average 28 drops, having a diameter of 80 μm, are applied to every $cm^2$. After different drying time larvae of potato beetle (Leptinotarsa decemlienata SAY) of third larval stage are placed onto the treated surfaces and 5 hours later the number of the intoxicated, ataxic larvae are determined. Four replicates, each using 15 larvae, are carried out. The results obtained and expressed in percentage are summarized in Table 1.

TABLE 1

| Drying time after the spraying (min) | Control* | Ex 1 | Ex 3 | Ex 5 | Ex 6 | Ex 8 | Ex 10 |
|---|---|---|---|---|---|---|---|
| | | Compositions according to knockdown % | | | | | |
| 0 | 0 | 70 | 100 | 70 | 75 | 100 | 100 |
| 20 | 0 | 20 | 80 | 35 | 30 | 100 | 100 |
| 120 | 0 | 0 | 50 | 5 | 0 | 85 | 90 |

*Composition according to Example 1, containing no active ingredient

Example 13

Activity on the worms of fulvous clover

The treatments are carried out as described in Example 12, except that sunflower leaves are used. After the different drying times worms of fulvous clover (Heliothis maritima GRASLIN) of $L_3$–$L_4$ larval stage, collected on field, are placed onto the treated leaves and 5 hours later the mortality is determined. The treatments are carried out in two replicates, each using 20 larvae. The results obtained are summarized in Table 2.

TABLE 2

| Drying time after the spraying (min) | Control* | Ex 1 | Ex 3 | Ex 5 | Ex 6 | Ex 8 | Ex 10 |
|---|---|---|---|---|---|---|---|
| | | Compositions according to knockdown % | | | | | |
| 0 | 0 | 90 | 100 | 100 | 100 | 100 | 100 |
| 20 | 0 | 30 | 100 | 35 | 40 | 100 | 100 |
| 120 | 0 | 0 | 65 | 0 | 0 | 100 | 100 |

*Composition according to Example 1, containing no active ingredient.

Example 14

Activity against plant-lice

The activity of the composition according to Example 3 is tested in industrial scale in a 10 ha plot on winter wheat against plant lice.

A commercial composition, DECIS ULV is used as comparative composition. The application was carried out from helicopter at the time of milky stage (milky ripening) (at June 22) using a special ULV head. The evaluation was carried out according to the Banks scale 2 and 7 days after the treatment using 8×25 marked ears. On the basis of the scale values the infection was calculated, thereafter the average number of the living individuals was expressed by the aid of an empirical table. The calculation of the percentage efficacy was made by the Henderson-Tilton equation.

TABLE 3

| Treatment | dose l/ha | Number of the living individuals: before treatment | 2 days after treatment | 7 days after treatment | efficacy in % (Henderson-Tilton) 2. day | 7. day |
|---|---|---|---|---|---|---|
| CYPERIL-S* | 1.5 | 30.1 | 0.9 | 0.5 | 97.0 | 80.3 |
| DECIS ULV | 1.5 | 30.8 | 1.4 | 1.0 | 95.6 | 62.7 |
| Untreated | — | 26.9 | 28.0 | 2.4 | — | — |

TABLE 3-continued

| Treatment | dose l/ha | Number of the living individuals before treatment | 2 days after treatment | 7 days after treatment | efficacy in % (Henderson-Tilton) 2. day | 7. day |
|---|---|---|---|---|---|---|
| control | | | | | | |

*Composition according to Example 3.

Example 15

To a measuring flask of 1000 ml 400 g of Phosalone and 25 g of nonylphenol polyglycol ether (EO=10) are added and filled up to 1000 ml with the 1:1:5 mixture (v/v) of Solvesso 200, Exxsol D 100 TM and sunflower oil. The mixture obtained is homogenized at 25° C.

The contact angle is determined as described in Example 1.

| Wetting time | Contact angle lucerne | sunflower |
|---|---|---|
| 0. minute | 18° | 22° |
| 20. minute | 8° | 18° |
| 120. minute | 6° | 7° |

Example 16

According to Example 15 the following composition is prepared:

| | | |
|---|---|---|
| Phenitrothion | 300 | g/l |
| Nonylphenol polyglycol ether (EO = 8) | 50 | g/l |
| Exxsol D 100 TM | 250 | g/l |
| Sunflower oil to | 1000 | ml |

The contact angle of the above preparation is determined as described in Example 1.

| Wetting time | Contact angle lucerne | sunflower |
|---|---|---|
| 0. minute | 22° | 24° |
| 20. minute | 7° | 15° |
| 120. minute | 4° | 6° |

Example 17

| | | |
|---|---|---|
| Malathion | 300 | g/l |
| Nonylphenol polyglycol ether | 25 | g/l |
| Solvesso 200 | 100 | g/l |
| Exxsol D 100 TM | 250 | g/l |
| Sunflower oil to | 1000 | ml |

The composition is prepared according to Example 15 and the contact angle is determined as described in Example 1.

| Wetting time | Contact angle lucerne | sunflower |
|---|---|---|
| 0. minute | 18° | 21° |
| 20. minute | 6° | 15° |
| 120. minute | 3° | 7° |

Example 18

| | | |
|---|---|---|
| Phosalone | 400 | g/l |
| Chinmix | 8 | g/l |
| Nonylphenol polyglycol ether (EO = 10) | 15 | g/l |
| Essxol D 100 TM | 250 | g/l |
| Sunflower oil to | 1000 | ml |

The composition is prepared according to Example 15 and the contact angle is determined as described in Example 1.

| Wetting angle | Contact angle lucerne | sunflower |
|---|---|---|
| 0. minute | 18° | 20° |
| 20. minute | 7° | 16° |
| 120. minute | 3° | 7° |

Example 19

| | | |
|---|---|---|
| Deltamethrin | 5 | g/l |
| Nonylphenol polyglycol ether (EO = 10) | 20 | g/l |
| Solvessso 200 | 100 | g/l |
| Exxsol D 100 TM | 250 | g/l |
| Sunflower oil to | 1000 | ml |

The composition is prepared according to Example 15 and the contact angle is determined as described in Example 1.

| Wetting time | Contact angle lucerne | sunflower |
|---|---|---|
| 0. minute | 17° | 18° |
| 20. minute | 7° | 12° |
| 120. minute | 3° | 9° |

Example 20

| | | |
|---|---|---|
| Malathion | 300 | g/l |
| Deltamethrin | 5 | g/l |
| Nonylphenol polyglycol ether (EO = 8) | 20 | g/l |
| Solvesso 200 | 100 | g/l |
| Exxsol D 100 TM | 250 | g/l |
| Sunflower oil to | 1000 | ml |

The composition is prepared according to Example 15 and the contact angle is determined as described in Example 1.

| Wetting time | Contact angle lucerne | sunflower |
|---|---|---|
| 0. minute | 21° | 24° |
| 20. minute | 8° | 15° |
| 120. minute | 4° | 8° |

What we claim is:

1. An ultra-low volume plant-protecting arthropodicidal formulation, which comprises:

(a) 0.5 to 30 g/l of a pyrethroid selected from the group consisting of allethrin, bifenthrin, bioallethrin, bioresmethrin, a mixture in a ratio of 40:60 of the following isomers of cypermethrin: 1RcisS+1-ScisR:1RtransS+1StransR, cyfluthrin, cyhalothrin, cypermethrin, deltamethrin, fenpropethrin, fenvalerate, flycythrinate, fluvalinate, permethrin, phenothrin, resmethrin, tetramethrin, tralomethrin, and transmix;

(b) 2 to 100 g/l of a nonylphenol polyglycol ether having an EO of 6 to 10;

(c) 2 to 300 g/l of a $C_{10}$ to $C_{15}$ aliphatic hydrocarbon mixture containing 45 to 50% naphthene and having a flash point of 50° to 100° C.; and (d) balance sunflower oil to 1000 ml, wherein the initial contact angle of the formulation on the plant surface is greater than 13°; after 20 minutes, is greater than 6°; and after 120 minutes is still at least 2°.

2. The ULV plant-protecting arthropodicidal formulation defined in claim 1 which comprises contamination-free, double-filtered sunflower oil.

3. The ULV plant-protecting arthropodicidal formulation defined in claim 1 which further comprises; 0.5 to 300 g/l of a phosphoric acid ester, thiophosphoric acid ester, or dithiophosphoric acid ester.

4. The ULV plant-protecting arthropodicidal formulation defined in claim 3 wherein the phosphoric acid ester is selected from the group consisting of trichlorforn, propaphos, dicrotophos, phosphamidon, profenophos, and crotophos; the thiophosphoric acid ester is selected from the group consisting of acephate, parathion, methylparathion, chlorpyriphos, demeton, oxydemethon-methyl, fenitrothion, EPN, triazophos, pirimiphos-methyl, mevinphos, quinalphos, and fenthion; and the dithiophosphopric acid ester is selected from the group consisting of dimethoate, azinphos-methyl, azinphos-ethyl, phosmet, malathion, phentoate, methidathion, and phosalone.

5. An ultra-low volume plant-protecting arthropodicidal formulation, which comprises:

(a) 0.75 to 10 g/l of a pyrethroid selected from the group consisting of a mixture in a ratio of 40:60 of the following isomers of cypermethrin: 1RcisS+1-ScrisR:1RtransS+1StransR, cypermethrin, deltamethrin, permethrin, tetramethrin, and transmix;

(b) 15 to 60 g/l of a nonylphenol polyglycol ether having an EO of 6 to 10;

(c) 5 to 250 g/l of a $C_{10}$ to $C_{15}$ aliphatic hydrocarbon mixture containing 45 to 50% naphthene and having a flash point of 50° to 100° C.; and (d) balance sunflower oil to 1000 ml, wherein the initial contact angle of the formulation on the plant surface is greater than 13°; after 20 minutes, is greater than 6°; and after 120 minutes is still at least 2°.

6. The ULV plant-protecting arthropodicidal formulation defined in claim 5 which further comprises a compound selected from the group consisting of quinalphos, phosalone and malathion.

7. The ULV plant-protecting arthropodicidal formulation defined in claim 5 which comprises:

(a) 7.5 g/l of a mixture in a ratio of 40:60 of the following isomers of cypermethrin: 1RcisS+1-ScisR:1Rtrans+1StransR;

(b) 60 g/l of nonylphenol polyglycol ether having an EO equalling 8;

(c) 250 g/l of a $C_{10}$ to $C_{15}$ hydrocarbon mixture containing 45 to 50% naphthene having a flash point higher than 58° C.; and (d) balance sunflower oil up to 1000 ml.

8. A plant protection method which comprises spraying onto plants a pesticidally effective amount of the ultra-low volume plant-protecting arthropodicidal formulation defined in claim 1.

* * * * *